(12) United States Patent
Chang et al.

(10) Patent No.: US 11,291,683 B2
(45) Date of Patent: Apr. 5, 2022

(54) BILAYER TABLETS OF B VITAMINS AND PROCESS FOR PREPARING THE SAME

(71) Applicant: Access Business Group International LLC, Ada, MI (US)

(72) Inventors: David S. Chang, Fullerton, CA (US); Dawna Venzon, Brea, CA (US); Shilpa Raut, Fullerton, CA (US); Allí Klosner, Fullerton, CA (US); Janjira Intra, Rowland Heights, CA (US); Edward S. Kahler, Anaheim, CA (US)

(73) Assignee: ACCESS BUSINESS GROUP INTERNATIONAL LLC, Ada, MI (US)

( * ) Notice: Subject to any disclaimer, the term of this patent is extended or adjusted under 35 U.S.C. 154(b) by 376 days.

(21) Appl. No.: 15/471,619

(22) Filed: Mar. 28, 2017

(65) Prior Publication Data

US 2017/0281666 A1  Oct. 5, 2017

Related U.S. Application Data

(60) Provisional application No. 62/316,867, filed on Apr. 1, 2016.

(51) Int. Cl.

| *A61K 31/714* | (2006.01) |
| *A61K 9/20* | (2006.01) |
| *A61K 36/064* | (2006.01) |
| *A61K 31/525* | (2006.01) |
| *A61K 31/4188* | (2006.01) |
| *A61K 31/455* | (2006.01) |
| *A61K 31/4415* | (2006.01) |
| *A61K 31/197* | (2006.01) |
| *A61K 31/51* | (2006.01) |
| *A61K 9/24* | (2006.01) |
| *A61K 31/519* | (2006.01) |
| *A61K 47/38* | (2006.01) |

(52) U.S. Cl.
CPC ............ *A61K 31/714* (2013.01); *A61K 9/209* (2013.01); *A61K 31/197* (2013.01); *A61K 31/4188* (2013.01); *A61K 31/4415* (2013.01); *A61K 31/455* (2013.01); *A61K 31/51* (2013.01); *A61K 31/519* (2013.01); *A61K 31/525* (2013.01); *A61K 36/064* (2013.01); *A61K 47/38* (2013.01)

(58) Field of Classification Search
None
See application file for complete search history.

(56) References Cited

U.S. PATENT DOCUMENTS

| 6,207,190 B1 | 3/2001 | Richardson et al. |
| 6,399,086 B1 | 6/2002 | Katzhendler et al. |
| 6,488,956 B1 * | 12/2002 | Paradissis ............. A61K 33/30 424/439 |
| 7,438,936 B2 * | 10/2008 | Huang ................. A61K 36/185 424/725 |
| 2004/0247677 A1 | 12/2004 | Oury et al. |
| 2006/0251722 A1 | 11/2006 | Bandak et al. |
| 2008/0063609 A1 | 3/2008 | Nissen |
| 2012/0027856 A1 | 2/2012 | Asmussen et al. |
| 2012/0269869 A1 | 10/2012 | Farrell |
| 2014/0178347 A1 | 6/2014 | Chang et al. |

FOREIGN PATENT DOCUMENTS

| CN | 1087517 A | 6/1994 |
| CN | 101795676 A | 8/2010 |
| DE | 20 2011 109556 U1 | 10/2012 |
| EP | 0 595 005 A1 | 5/1994 |
| JP | 2010-536903 A | 12/2010 |
| WO | WO 2005/115348 | * 12/2005 |
| WO | WO 2017/173031 | 10/2017 |

OTHER PUBLICATIONS

Joseph, JA, "Formulation Challenges: Multiple Vitamin and Mineral Dosage Forms," *Pharmaceutical Dosage Forms: Tablets, vol. 2 Rational Design and Formulation*, CRC Press (2008).
Arcot, I and Shrestha, A, "Folate: Methods of Analysis," *Trends in Food Science and Technology*, 16:253-266 (2005).
Nokhodchi, A, "The Role of Oral Controlled Release Matrix Tablets in Drug Delivery Systems," *BioImpacts* 2(4):175-187 (2012).
The Merck Index, "An Encyclopedia of Chemicals, Drugs, and Biologicals," $10^{th}$ Ed, Merck & Company, Rahway, NJ (1983).
Eitenmiller, RR, et al., "Vitamin Analysis for the Health and Food Sciences," CRC Press, Taylor & Francis Group, Boca Raton (2008).
Ball, GFM, "Vitamins in Food: Analysis, Bioavailability and Stability," CRC Press, Taylor & Francis Group, Boca Raton FL, vol. 156 (2006).
Zempleni, J, et al., "Handbook of Vitamins," $4^{th}$ Ed, CRC Press, Taylor & Francis Group, Boca Raton (2007).
Zielinska-Dawidziak, M, et al., "Transport of High Concentration of Thiamin, Riboflavin and Pyridoxine Across Intestinal Epithelial Cells Caco-2," *J Nutr Sci Vitaminol*, 54:423-429 (2008).
International Search Report and Written Opinion received in PCT Application No. PCT/US2017/024927 dated Jun. 22, 2017.
United States Pharmacopeia and National Formulary, "In Vitro and In Vivo Evaluation of Dosage Forms," *USP 26-NF 21*, United States Pharmacopeial Convention, Inc., Rockville, MD (2002).
U.S. Department of Health and Human Services, Food and Drug Administration, Center for Drug Evaluation and Research (CDER), "Guidance for Industry, Extended Release Oral Dosage Forms: Development, Evaluation, and Application of In Vitro/In Vivo Correlations," U.S. Government Printing Office, Washington DC (Sep. 1997).

(Continued)

*Primary Examiner* — Tigabu Kassa
(74) *Attorney, Agent, or Firm* — Crowell & Moring LLP

(57) ABSTRACT

Compositions for oral administration and processes of preparing the same are described. In particular, compositions in the form of bilayer tablets including B vitamins for modified delivery are described. The bilayer multi-B vitamin tablets offer immediate release of a first set of B vitamins, such as riboflavin (B2) and cyanocobalamin (B12) followed by controlled release of a second set of B vitamins, such as folic acid, biotin, niacinamide (B3), pyridoxine (B6), pantothenic acid (B5) and thiamine (B1).

20 Claims, 7 Drawing Sheets

(56) References Cited

OTHER PUBLICATIONS

United States Pharmacopeial Convention, Inc., USP, Chapter 2040, Rockville, MD (2002).
United States Pharmacopeial Convention, Inc., USP, Chapter 711, Rockville, MD (2002).
Notification Concerning Transmittal of International Preliminary Report on Patentability (Chapter 1 of the Patent Cooperation Treaty) dated Oct. 11, 2018, and the accompanying International Preliminary Report of Patentability dated Oct. 2, 2018, issued in connection with the corresponding International Application No. PCT/US2017/024927.
Extended European Search Report received in European Application No. 17776623.5-1106/3435788 dated Nov. 11, 2019.
Examination Report received in the corresponding European Application No. 17776623.5, dated Aug. 17, 2020, and an email dated Aug. 25, 2020 received from European associate enclosing the Examination Report.
Examination Report received in the corresponding Indian Application No. 201817033729, dated Jul. 6, 2020 (with English translation), and an email dated Jul. 31, 2020 received from Indian associate enclosing the Examination Report.
Reporting letter dated Oct. 12, 2020 received from Japanese associate enclosing first Office Action received in Japanese Application No. JP 2018-551202 dated Sep. 23, 2020.
Office Action received in Japanese Application No. JP 2018-551202 dated Sep. 23, 2020 (including English translation).
Reporting Email dated May 13, 2021 received from Taiwanese associate enclosing Official Letter and Search Report received in Taiwanese Application No. 106111155.
Official Letter and Search Report received in Taiwanese Application No. 106111155 dated May 13, 2021.
English translation of Official Letter and Search Report from TIPO received in Taiwanese Application No. 106111155, as provided with email communication dated Jun. 10, 2021.
First Office Action received in Taiwanese Application No. 106111155, dated Aug. 31, 2021 (in Taiwanese), and Reporting Email dated Aug. 31, 2021 forwarding the First Office Action.
Reporting Letter dated Oct. 1, 2021 providing detailed report in English of the First Office Action dated Aug. 31, 2021 received in Taiwanese Application No. 106111155.

* cited by examiner

BILAYER TABLETS OF B VITAMINS AND PROCESS FOR PREPARING THE SAME

RELATED APPLICATIONS

The present patent document claims the benefit of the filing date under 35 U.S.C. § 119(e) of Provisional U.S. patent application Ser. No. 62/316,867, filed Apr. 1, 2016, which is hereby incorporated by reference.

BACKGROUND

Compositions for oral administration and processes of preparing the same are described. In particular, compositions in the form of bilayer tablets including B vitamins for modified or controlled delivery to a subject are described. The bilayer multi-B vitamin tablets offer immediate release of a first set of B vitamins, such as riboflavin (B2) and cyanocobalamin (B12) followed by modified release of a second set of B vitamins, such as folic acid, biotin, niacinamide (B3), pyridoxine (B6), pantothenic acid (B5), and thiamine (B1), as supplements.

An adequate intake of vitamins and minerals is important for health and can be obtained through a healthy diet. In the absence of such a diet, dietary supplements may be useful sources of one or more of these micronutrients that otherwise might be consumed in less than recommended amounts. Supplemental vitamins and minerals may also be required when gastrointestinal absorption is impaired, where there are excessive losses, or increased requirements. For example, atrophic gastritis, in which stomach lining has thinned; pernicious anemia, which makes it hard for a body to absorb vitamin B12; surgery that removed part of stomach or small intestine, including weight loss surgery; conditions affecting the small intestine, such as Crohn's disease, celiac disease, bacterial growth, or a parasite; heavy drinking; immune system disorders, such as Graves' disease or lupus; long-term use of acid-reducing drugs, all contribute to B vitamin deficiency and an increase in micronutrient needs. Consequences of deficiency of one or more vitamins or minerals can be serious.

In addition, there are often factors that can contribute to inadequate absorption of vitamins and minerals. For example, Vitamin B12, when administered in a timed-release format, is not absorbed well. Vitamin B12 must bind to an intrinsic factor to be absorbed by the body. Because the intrinsic factor is only released from the parietal cells located in the stomach wall, free B12 must be available within the stomach to form a complete B12-intrinsic factor complex necessary for absorption. Thus, when B12 is delivered as a time release product, this nutrient may not release completely in the stomach and upper duodenum, resulting in incomplete absorption and waste of the nutrient.

The time release products currently on the market use high amounts of polymers to achieve the time release profile. For example, manufacturers have used hydrophilic hydrocolloid gelling polymers such as hydroxypropyl methylcellulose, hydroxypropyl cellulose, or Pullulan to formulate sustained release tablets or capsules. These polymers first form a gel when exposed to an aqueous environment of low pH thereby slowly diffusing the active medicament which is contained within the polymer matrix. When the gel enters a higher pH environment such as that found in the intestines, however, it dissolves resulting in a less controlled drug release. To provide better sustained release properties in higher pH environments, some pharmaceutical manufacturers use polymers which dissolve only at higher pHs, such as acrylic resins, acrylic latex dispersions, cellulose acetate phthalate, and hydroxypropyl methylcellulose phthalate, either alone or in combination with hydrophilic polymers.

Generally, these formulations are prepared by combining the medicament with a finely divided powder of the hydrophilic polymer, or the hydrophilic and water-insoluble polymers. These ingredients are mixed and granulated with water or an organic solvent and the granulation is dried. The dry granulation is then usually further blended with various pharmaceutical additives and compressed into tablets.

Although these types of formulations have been successfully used to manufacture dosage forms which demonstrate sustained release properties, these formulations generally do not have the desired release profile or serum concentration of medicament over an extended period of time. Also, having polymers can be undesirable when trying to include mainly natural ingredients within a product.

There is a need for multi-layer formulations that can deliver B vitamins in a timed-release format at the suitable locations in the body using natural products as excipients, alone or in combination with other suitable excipients.

SUMMARY

Certain embodiments relate to a bilayer multi-active formulation comprising a first layer comprising basic yeast and a first set of active components, the first layer providing immediate release of the first set of active components at a first location in the gastrointestinal tract; a second layer comprising basic yeast and a second set of active components, the second layer providing a modified release of the second set of active components at a second location in the gastrointestinal tract; wherein the basic yeast from the first layer contributes to the modified release of the second set of active components from the second layer; and optionally, a film coating that covers the first layer and the second layer.

Certain other embodiments relate to a bilayer multi-B vitamin formulation comprising a first layer comprising basic yeast and a first set of B vitamins comprising riboflavin (B2) and cyanocobalamin (B12), the first layer providing immediate release of the first set of B vitamins at a first location in the gastrointestinal tract; a second layer comprising basic yeast and a second set of B vitamins selected from the group consisting of folic acid, biotin, niacinamide (B3), pyridoxine (B6), pantothenic acid (B5), thiamine (B1), and a combination thereof, the second layer providing a modified release of the second set of B vitamins at a second location in the gastrointestinal tract, wherein the basic yeast from the first layer contributes to the modified release of the second set of B vitamins from the second layer; and optionally, a film coating that covers the first layer and the second layer. In the bilayer multi-B vitamin formulation, the basic yeast modulates the dissolution profile of the folic acid from the formulation. In the bilayer multi-B vitamin formulation, the modified release of the second set of B vitamins from the second layer is over a period of 8 hours. In the bilayer multi-B vitamin formulation, the formulation is for oral delivery and may be in a form of a tablet. In the bilayer multi-B vitamin formulation, the B vitamins are present in amounts within the range from about 0.01 mg to 1000 mg in single or divided doses. The bilayer multi-B vitamin formulation may comprise 1-5 mg of B1, 1-10 mg of B2, 15-30 mg of B3, 5-30 mg of B5, 1-5 mg of B6, 200-500 μg of folic acid, 20-200 μg of biotin, and 1-10 μg of B12. The amount of the basic yeast in the first layer may be in the range of about 1-99%. The amount of the basic yeast in the second layer may be in the range of about 1-99%. In the bilayer multi-B vitamin formulation, upon hydration of a surface of the formulation a viscous gel layer forms at the surface. In the bilayer multi-B vitamin formulation, the first and second layers each comprise abutting substantially planar layers, which form the bilayer tablet. The first location in the gastrointestinal tract may be selected from the group consisting of the stomach, the duodenum, the small intestine, and the large intestine. The second location in the gastrointestinal tract may be selected from the group consisting of the stomach, the duodenum, the small intestine, and the large intestine. The first and the second locations in the gastrointestinal tract may be the same or different.

Certain further embodiments relate to a method for preventing or treating a vitamin B deficiency comprising administering the bilayer multi-B vitamin formulation of the present invention to a subject.

Certain additional embodiments relate to a modified release tablet comprising a first layer comprising basic yeast and a first set of B vitamins comprising riboflavin (B2) and cyanocobalamin (B12), the first layer providing immediate release of the first set of B vitamins at a first location in the gastrointestinal tract; a second layer comprising basic yeast and a second set of B vitamins selected from the group consisting of folic acid, biotin, niacinamide (B3), pyridoxine (B6), pantothenic acid (B5), thiamine (B1), and a combination thereof, the second layer providing a modified release of the second set of B vitamins at a second location in the gastrointestinal tract, wherein the basic yeast from the first layer contributes to the modified release of the second set of B vitamins from the second layer; and optionally, a film coating that covers the first layer and the second layer.

Certain further embodiments relate to a dietary supplement comprising a bilayer multi-active formulation comprising a first layer comprising a basic yeast and a first set of active components, the first layer providing immediate release of the first set of active components at a first location in the gastrointestinal tract; a second layer comprising a basic yeast and a second set of active components, the second layer providing a modified release of the second set of active components, wherein the basic yeast from the first layer contributes to the modified release of the second set of the active components from the second layer at a second location in the gastrointestinal tract; and optionally, a film coating that covers the first layer and the second layer.

Certain further embodiments relate to the use of basic yeast as a rate-controlling natural polymer in a tablet formulation. The tablet formulation may be a bilayer tablet formulation described herein. Alternatively, the tablet formulation may be a single-layer tablet formulation. The basic yeast modulates the dissolution profile of the formulation components from the tablet.

DETAILED DESCRIPTION

Figure 1:
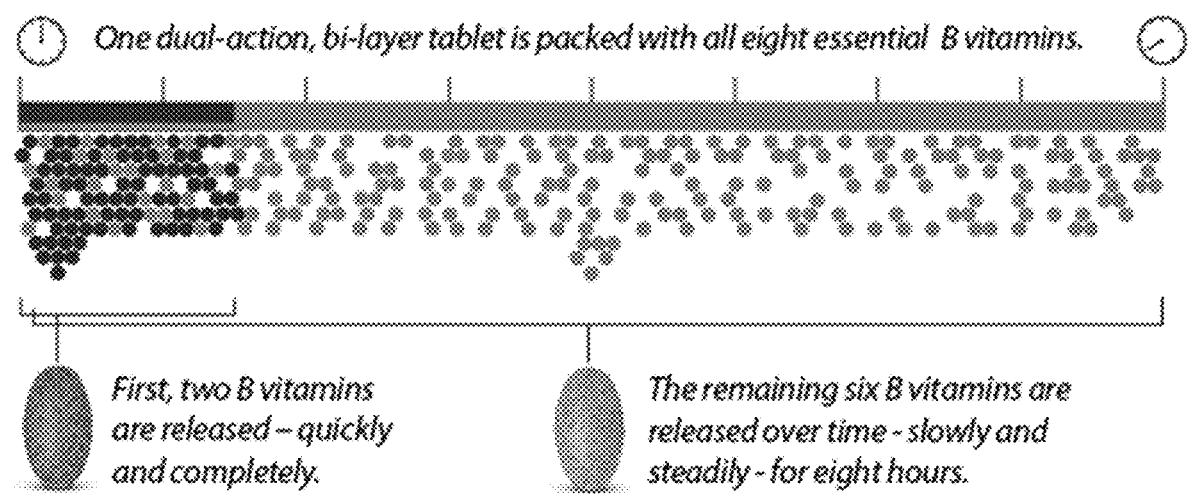
FIG. 1 shows a schematic illustration of the bi-layered dual-release from Vitamin B Complex supplement.

The following definitions are used to describe the various aspects and characteristics of the claimed formulations and processes.

The term "immediate release" means that the release of the components from the tablet is not delayed once at its intended location, e.g., the rapid break-up and delivery of a portion of the tablet in the upper gastrointestinal tract.

The term "modified release" is intended to exclude immediate release and to encompass controlled release, extended release, pulsed release, sustained release, delayed release, timed release, variable release and combinations thereof. These terms may be used interchangeably.

The term "extended release" denotes the duration of time between administration of the composition and the release of the components from a particular layer.

The term "sufficient amounts" means that the amounts meet the currently accepted recommended dietary allowances and intakes for humans.

An "active" refers to any drug, medicine, supplement, such as a vitamin or a mineral supplement.

The term "label claim" refers to the amount of specific vitamin that is listed on the product label.

Formulations

Certain embodiments relate to the delivery of B vitamins from oral tablet supplements. These embodiments relate to the timely release of the B vitamins.

Vitamins B2 and B12 are made by bio-fermentation; other B vitamins are synthetic and are commercially available. These materials are obtained as powders or triturates, and are blended in-house to form a tablet with other excipients.

The advantages of the delivery is that the modified or controlled release of a mixed vitamin B formulation helps to limit the waste associated with large, instant release dosages by minimizing the saturation of and competition for those critical vitamin B transporters within the small intestine. As such, the described delivery systems and formulations are designed as a bilayer tablet with a first layer providing an immediate release of B2 and B12 and a second layer consisting of the remaining six B vitamins (folic acid, biotin, niacinamide (B3), pyridoxine (B6), pantothenic acid (B5), and thiamine (B1)), providing for a modified release of the B vitamins over a period of at least 8 hours.

A multi-component delivery system (i.e., a bilayer tablet) that is useful for administering varying dosage levels of B vitamins immediately and under modified release is described. The multi-component delivery system described herein is especially useful for administering B vitamins to people with vitamin B deficiencies due to disease, malnutrition or other causes. The multi-component delivery system employs the basic yeast in addition to or instead of the commonly used pharmaceutically-acceptable excipients, such as controlled-release polymers.

Basic yeast (i.e., yeast or natural yeast, terms may be used interchangeably) is natural and can be a source of amino acids and minerals. Basic yeast is not fortified. For example, basic yeast may be whole yeast of, e.g., *S. cerevisiae*. In contrast, commonly used excipients in modified release products are typically nonnutritive manufactured polymers, such as hydroxypropyl methylcellulose (HPMC), polyethylene oxide (PEO), hydroxyethyl cellulose, polyacrylic acid, etc. The basic yeast used as a natural excipient in the described formulations contributes to the modified and extended release of the B vitamins from the bilayer tablet. Surprisingly, it was observed that the yeast in the immediate release layer affected the release of folic acid in the modified release layer. This is the first instance showing the effect of basic yeast on the dissolution profile of folic acid from multi-B vitamin modified release tablet. The data provided below further details the effect of yeast (present in the immediate release layer) on the release profile of folic acid. Surprisingly, the data show that natural nutritive excipients, such as the basic yeast can be safely used to enhance the slow release of active by other commonly used polymer materials to achieve modified/controlled time release. The use of basic yeast also helps to keep the polymer levels low and yet obtain the desired time release profile.

In certain embodiments, basic yeast can be used as a rate controlling natural polymer independently from the described bilayer tablet formulations; specifically, basic yeast can be used as rate controlling natural polymer in a single layer, typical tablet formulations. The basic yeast modulates the dissolution profile of the formulation components from the tablet formulation.

In certain embodiments, by utilizing basic yeast in combination with the commonly used polymers a desired time release profile can be attained, which is synergistic. This technology achieves the desired results by utilizing lower amounts of both ingredients. For example, while the current recommendations are to use at least 20% polymer to achieve consistent controlled release profile, surprisingly, as described herein to achieve desired release profile, only 12-15% of polymer was needed in combination with the basic yeast. It is believed that even lower amount (<12-15%) of polymer may also be used. Details of a study showing the amount of polymer required to achieve similar release as with a formula with yeast are provided below.

The described delivery system or formulations have a first layer providing immediate release of a first set of components at a first location in the gastrointestinal tract, and includes basic yeast and a first set of B vitamins, riboflavin (B2), cyanocobalamin (B12), each at a sufficient amount and in a form absorbable at the first location. The first location is selected from the group consisting of the stomach and the duodenum.

The delivery system also has a second layer comprising basic yeast and a second set of B vitamins selected from the group consisting of folic acid, biotin, niacinamide (B3), pyridoxine (B6), pantothenic acid (B5), thiamine (B1), and a combination thereof, each at a sufficient amount and in a form absorbable at a second location, where the second layer provides modified release of the second set of B vitamins at the second location in the gastrointestinal tract, the second location being the same as the first location, further downstream in the gastrointestinal tract than the first location, or both. The modified release of the second set of B vitamins from the second layer is slow (i.e., over the course of 8 hours). The modified release of the second set of B vitamins from the second layer is affected by the basic yeast from the immediate release layer.

The second location is selected from the group consisting of the duodenum, small and large intestines. The second location may be the same (e.g., there may be some overlap in the lower duodenum) or may be different from the first location in the gastrointestinal tract.

The modified release of these six B vitamins minimizes saturation of transporters by keeping gut lumen concentrations low enough to utilize active transport over the less-efficient and wasteful passive transport, thereby supporting efficient absorption through the gut wall to reach the blood stream. Also, it is known that biotin (B7) and pantothenic acid (B5) utilize the same sodium dependent carrier-mediated uptake mechanism in the intestine, so minimizing saturation of that system prevents competitive inhibition by the two vitamins. The present formulations make it possible to release the six B vitamins slowly (i.e., over a period of 8 hours), supporting efficient absorption and limiting nutrient waste associated with larger doses.

To maximize absorption efficiency, the two layers provide dual action with the immediate release layer providing instant release of riboflavin and B12, and the modified release (e.g., modified release layer) providing a modified release of folic acid, biotin, niacinamide, pyridoxine, pantothenic acid and thiamine.

The separation of these nutrients overcomes some of the disadvantages identified with the current vitamin B products as well as some disadvantages, which are only recently identified. It is important for B12 to be released early so it may bind with intrinsic factor in the stomach and duodenum for subsequent ileal absorption, so it is necessary to include this vitamin in the immediate release layer. Additionally, studies described below, within simulated gastrointestinal conditions have shown that B2 is best released when in an immediate release formulation, while maintaining lumen concentrations supporting active transporter kinetics for efficient physiological absorption across the gut wall. For this reason, the B2 is also included in the immediate release layer.

Specifically, the data presented below show that the riboflavin (B2) releases best when incorporated in the immediate release layer instead of the modified release layer of the formulation. The immediate and modified release formulations were tested individually to determine the release profile in a dynamic computer-controlled in vitro system simulating the human upper gastrointestinal tract (TIM-1 system). The data (Example 2) showed higher bioaccessibility of B2 from the immediate release tablets (79% for low dose and 89% for high dose) vs. the modified release tablets (42% for low dose and 56% for high dose), as shown in Table 4. It was also found that B2 had a high percentage of vitamin remaining in the tablet after the course of the 5 hour study, which was especially evident in the low dose formula as 48.2% of the riboflavin was still remaining (Table 5). From the data, it was concluded that the B2 was best released when incorporated as an instant release nutrient. In support of this design element, peak gut lumen concentrations from instantly released riboflavin remain under measured maximal riboflavin transporter kinetics so efficiency of absorption of this vitamin is maintained by being included in the instant release layer. Maximal vitamin B2 concentration was measured in the TIM-1 system to be approximately 2 micromolar at time 60-120 minutes, which is well below any published research demonstrating a maximal permeability concentration for active transport of vitamin B2 at less than 25 micromolar (Zielinska-Dawidziak M, et al. Transport of high concentration of thiamin, riboflavin and pyridoxine across intestinal epithelial cells caco-2. J Nutr Sci Vitaminol 54:423-429, 2008).

One advantage of separating the vitamin B components into layers is that it allows control of the release from the layers at a time and location that corresponds to the location of optimal absorption in the gastrointestinal tract. This separation of B vitamin components limits the potential for unwanted binding to food and other particles that may reduce the bioavailability of the vitamin B components. By separating various components in the different layers of the composition, they can aid each other to optimize absorption, and keep the interference of components in the gastrointestinal tract minimized.

Another advantage of separating the vitamin B components into layers is that the modified release of a mixed vitamin B formulation helps to limit the waste associated with large, instant release dosages by minimizing the saturation of the competition for those critical vitamin B transporters within the small intestine.

The formulations will contain B vitamins (riboflavin (B2), cyanocobalamin (B12), folic acid, biotin, niacinamide (B3), pyridoxine (B6), pantothenic acid (B5) and thiamine (B1)), each in an amount as normally employed for such Vitamins and, as exemplified in the U.S. Recommended Dietary Allowances (RDAs). For example, the B vitamins may be employed in amounts within the range from about 0.01 mg to 1000 mg per day in single or divided doses, and preferably from about 0.1 to about 500 mg per day.

The following formulation provided in Table 1 below, having an amount of each B vitamin in the range indicated, will provide one of several multi-B vitamin compositions that may be used to form a bilayer multi-B vitamin tablet:

TABLE 1

| B Vitamin | Amount | Units |
| --- | --- | --- |
| Thiamine (B1) | 1-5 | mg |
| Riboflavin (B2) | 1-10 | mg |
| Niacinamide (B3) | 15-30 | mg |
| Pantothenic acid (B5) | 5-30 | mg |
| Pyridoxine (B6) | 1-5 | mg |
| Folic acid | 200-500 | µg |
| Biotin | 20-200 | µg |
| B12 | 1-10 | µg |

In some embodiments, the weight ratio of B vitamins is 1%-99% relative to the weight of the bilayer formulation, which is conversely 1-99% excipients, such as basic yeast and/or polymers.

This weight ratio of B vitamins relative to the weight of the bilayer formulation may be at least about 1%, at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 16%, at least about 17%, at least about 18%, at least about 19%, at least about 20%, at least about 21%, at least about 22%, at least about 23%, at least about 24%, at least about 25%, at least about 26%, at least about 27%, at least about 28%, at least about 29%, at least about 30%, at least about 31%, at least about 32%, at least about 33%, at least about 34%, at least about 35%, at least about 36%, at least about 37%, at least about 38%, at least about 39%, at least about 40%, at least about 41%, at least about 42%, at least about 43%, at least about 44%, at least about 45%, at least about 46%, at least about 47%, at least about 48%, at least about 49%, at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least at least about 97%, at least about 98%, or at least about 99%.

The formulations will also contain excipients.

The weight ratio of the yeast/polymer relative to the weight of the bilayer formulation may be in the range of about 1-99%. The weight ratio of yeast/polymer relative to the weight of the controlled release layer in the bilayer formulation may be in the range of about 1-99%; the weight ratio of yeast/polymer relative to the weight of the immediate release layer in the bilayer formulation may be in the range of about 1-99%.

The commonly used polymers in time release products are typically nonnutritive manufactured polymers, such as hydroxypropyl methylcellulose, polyethylene oxide, hydroxyethyl cellulose, polyacrylic acid, etc. Basic yeast is natural and can be a source of some amino acids and minerals.

In certain embodiments, the basic yeast is used as a sole natural excipient in the described bilayer formulations. In such formulations, no polymers are used as excipients or additives.

In certain alternative embodiments, at least 15% hydroxypropyl methylcellulose polymer may be used in the controlled-release layer.

The basic yeast can be used in the immediate release layer, the modified release layer, or both. The amount of the basic yeast used can be the same or different in both layers. In certain embodiments, the amount of the basic yeast excipient in a formulation can be in the range of about 1-90%. In certain embodiments, the amount of the basic yeast excipient in the immediate release layer can be in the range of about 1-50%; the amount of the basic yeast excipient in the modified release layer can be in the range of about 1-50%. In certain other embodiments, the amount of the basic yeast excipient in the immediate release layer can be in the range of about 1-25% the amount of the basic yeast excipient in the modified release layer can be in the range of about 1-25%. In certain embodiments, the amount of the basic yeast excipient in the immediate release layer can be in the range of about 1-15%; the amount of the basic yeast excipient in the modified release layer can be in the range of about 1-15%.

As demonstrated in the examples below, the basic yeast contributed to the extended release of the B vitamins from the tablet. Surprisingly, it was observed that the basic yeast in the first or immediate release layer had an effect on the release of folic acid in the second or the modified release layer. The data provided below details the effect of the basic yeast (present in the first or immediate release layer) on the release profile of folic acid in the second layer. The data show the use of a natural nutritive excipient that can be used in place of other commonly used materials to achieve time release of the vitamin B components. Further advantage of using yeast is that it also helps to keep the polymer levels in the formulation low (as compared to the standard table formulations) and yet obtain the desired time release profile of the vitamin B components. Therefore, in certain embodiments, the basic yeast is the sole excipient in the formulation.

In certain embodiments, the delivery system may also include a polymer. Examples of polymers suitable to be included in the formulations with basic yeast include hydrophilic hydrocolloid gelling polymers such as hydroxypropyl methylcellulose, hydroxypropyl cellulose, polyethylene oxide, polyacrylic acid, or Pullulan. Other suitable polymers may also be included.

In certain embodiments, the delivery system may optionally include a film coating that covers the modified release layer and the immediate release layer.

In certain further embodiments, the delivery system may also include other non-vitamin B components, including other vitamins or minerals, or trace elements that are to be released at the first and or the second location(s). Specifically, in certain further embodiments, the immediate and or modified release layers may include other vitamins, such as A, C, E, D and K. In addition, one or more minerals and trace elements, including, but not limited to chromium, calcium, zinc, magnesium, molybdenum, selenium, copper and iodine, may be included in immediate and or modified release layers. Furthermore, other actives, such as phytonutrients (e.g., cartoneoids like betacarotne, lycopene, lutein, zeaxanthin, etc.), or flavonoids (e.g., catechins, hesperidin, quercetin, etc.), or ellagic acids (e.g., resveratrol), glucosinolates, phytoestrogens, or active pharmaceutical ingredients may be included. The components of the modified release layer will be released after the components of the immediate release layer, and at the same point and or a point downstream from the release of the components of the immediate release layer.

The delivery system described herein may also be used to deliver drugs, other active components, vitamins, minerals, etc.

Method of Making

In forming multi-B vitamin formulation in the form of a bilayer tablet, the immediate release layer containing riboflavin and B12 includes the basic yeast in an amount within the range from about 1 to about 90%, preferably from about 5 to about 85% by weight of the immediate release layer.

In addition, in certain embodiments, the immediate release layer may also include bulking agents, such as lactose, microcrystalline cellulose, wood cellulose, corn starch, modified corn starch, calcium phosphate, sugar, dextrose, mannitol or sorbitol. The basic yeast and or the bulking agent may be present in an amount from about 1 to about 90%, preferably from about 5 to about 85% by weight of the immediate release layer containing riboflavin and B12.

The modified release layer of the bilayer tablet containing folic acid, biotin, niacinamide (B3), pyridoxine (B6), pantothenic acid (B5) and thiamine (B1), and or a combination thereof will also include the basic yeast in an amount within the range from about 1 to about 90%, preferably from about 5 to about 85% by weight of the modified release layer.

In addition, the modified release layer may also include a bulking agent such as lactose, microcrystalline cellulose, modified corn starch, calcium phosphate or other bulking agent as set out above for the immediate release layer, in an amount within the range from about 1 to about 90%, preferably from about 5 to about 85% by weight of the modified release layer.

In certain embodiments, the immediate and modified release layers may also include a tableting lubricant, such as zinc stearate, magnesium stearate, calcium stearate, talc, carnauba wax, stearic acid, palmitic acid or hydrogenated vegetable oils and fats, in an amount within the range from about 0.01 to about 4%, and preferably 0.02 to about 2% by weight of each layer.

In addition, the layers may include a binder such as corn starch, pregelatinized starch, polyvinyl pyrrolidone (PVP), hydroxypropylmethyl cellulose (HPMC), ethyl cellulose, cellulose acetate and the like, in an amount within the range from about 0.5 to about 20%, preferably from about 1 to about 10% by weight of each layer, and a tableting lubricant such as magnesium stearate, zinc stearate, or other lubricant as set out above with respect to each layer in an amount from about 0.01 to about 4%, preferably from about 0.02 to about 2% by weight of each layer.

In forming the bilayer tablet, both layers may be prepared by conventional wet granulation or dry granulation (compaction) techniques, or any other technique known in the art.

The layers may then be compressed and combined to form a bilayer tablet employing conventional bilayer tableting equipment.

In certain embodiments, the immediate release and modified release layers each comprise abutting substantially planar layers, which form the bilayer tablet.

Other conventional ingredients that may optionally be present in either of the two layers include preservatives, stabilizers, anti-adherents or silica flow conditioners or glidants, such as Syloid brand silicon dioxide.

In certain embodiments, the bilayer tablet may also include an outer protective coating layer that may comprise from 0 to about 15% by weight of the bilayer tablet. The outer protective coating layer that is applied over the bilayer tablet may comprise any conventional coating formulations and will include one or more film-formers or binders, such as a hydrophilic polymer like hydroxy-propylmethyl cellulose (HPMC) and a hydrophobic polymer like ethyl cellulose, cellulose acetate, polyvinyl alcohol-maleic anhydride copolymers, acrylic copolymers, β-pinene polymers, glyceryl esters of wood resins and the like, and one or more plasticizers, such as polyethylene glycol, triethyl citrate, diethyl phthalate, propylene glycol, glycerin, butyl phthalate, castor oil and the like.

The film formers are applied from a solvent system containing one or more solvents including water, alcohols like methyl alcohol, ethyl alcohol or isopropyl alcohol, ketones like acetone, or ethylmethyl ketone, chlorinated hydrocarbons like methylene chloride, dichloroethane, and 1,1,1-trichloroethane.

Method of Administering

In carrying out the method of the present invention, the bilayer multi-B formulations containing a first set of vitamin B components comprising riboflavin (B2) and cyanocobalamin (B12) and a second set of vitamin B components comprising folic acid, biotin, niacinamide (B3), pyridoxine (B6), pantothenic acid (B5) and thiamine (B1) may be administered to mammalian species, such as monkeys, dogs, cats, rats, humans, etc. as a dietary supplement, and, as described hereinbefore, may be incorporated in tablet. In certain embodiments, the dosage forms will also include the necessary carrier material, excipient, lubricant, buffer, anti-bacterial, bulking agent (such as mannitol), anti-oxidants such as Vitamin C and Vitamin E, as well as minerals, sodium bisulfite, and the like.

The dose administered must be adjusted according to age, weight and condition of the subject, as well as the route of administration, dosage form and regimen and the desired result.

The compositions described above may be administered in the dosage forms as described above in single or divided doses of one to four times daily.

Tablets of various sizes can be prepared, e.g., of about 2 to 2000 mg in total weight, containing the B vitamins in the ranges described above, with the remainder being a physiologically acceptable carrier (e.g., basic yeast) or other materials according to accepted pharmaceutical practice.

The following Examples represent preferred embodiments of the present invention.

EXAMPLES

Example 1: The Effect of Basic Yeast on the Dissolution Profile of Folic Acid from Vitamin B Modified Release Tablet A. Formulation A bi-layered tablet was formulated containing all eight B vitamins namely B1, B2, B3, B5, B6, B7 B9 and B12. Layer 1 was formulated to release six B vitamins slowly over a period of 8 hours and layer 2 was designed to instantly release B2 and B12. The bi-layered formulations are illustrated in FIG. 1. HPMC was used as the controlled release polymer. During preliminary prototyping, it was found that the yeast in layer 2 had an effect on the release of B vitamins from layer 1.

B. Study

To investigate the effect of basic yeast on the dissolution profile of folic acid from vitamin B time release tablet, five formulas (Table 2) with different amounts of yeast were tested. The amount of yeast in the modified release layer was kept constant at 30 mg and included at least 15% hydroxypropyl methylcellulose (which acts as a controlled-release polymer).

Dissolution testing was performed using a qualified Sotax dissolution tester operated as USP Apparatus 2 (paddle) at 75 rpm and at 37±0.5° C. The media used for dissolution was different for different B vitamins and was selected to minimize degradation of these vitamins for the length of the study i.e. 8 hours. Each dissolution test was performed with 6 tablets. Sample aliquots were collected at 2, 4, 6, and 8 hour and filtered through 0.45-μm Millex-HV syringe filters, and analyzed by HPLC for dissolution samples.

TABLE 2

Percent Folic Acid dissolution from Bilayer time release multi-B vitamin tablets.

| Time (hr) | A1: no yeast in immediate release layer | A2: 30 mg Yeast in immediate release layer | A3: 60 mg Yeast in immediate release layer | A4: 90 mg Yeast in immediate release layer | A5: no yeast in both layers |
|---|---|---|---|---|---|
| 0 | 0 | 0 | 0 | 0 | 0 |
| 2 | 72.73 | 48.53 | 41.81 | 36.87 | 114 |
| 4 | 91.78 | 74.88 | 67.06 | 60.95 | 128 |
| 6 | 99.02 | 95.82 | 85.72 | 79.79 | 129.7 |
| 8 | 103.17 | 109.97 | 100.87 | 94.09 | 124.9 |

Based on USP XXXIX chapter 1088, extended-release tablets are formulated in such a manner as to make the active available over an extended period of time following ingestion (*In Vitro and In Vivo* Evaluation of Dosage Forms <1088>. In *United States Pharmacopeia and National Formulary USP 26-NF 21*; United States Pharmacopeial Convention, Inc.: Rockville, Md. (2002)).

There is no USP monograph available for vitamin B complex extended release tablets. Therefore, it is the responsibility of the formulation scientists to develop an appropriate in vitro dissolution protocol to determine stable release characteristics of the product over time. The dissolution media used were different for the different B vitamins to ensure stability of the vitamins for 8 hours during testing. There is a USP guideline for dissolution of extended-release dosage forms. The guideline indicates "For an extended-release dosage form, at least three test time points are chosen to characterize the in vitro drug release profile for Pharmacopeia purposes." An early time point (usually 1 to 2 hours) is chosen to show that there is little probability of dose dumping. An intermediate time point is chosen to define the in vitro release profile of dosage form, and a final time point is chosen to show the essentially complete release of the drug. Test times and specification are usually established on the basis of an evaluation of release profile data (Extended Release Oral Dosage Forms: Development, Evaluation, and Application of In Vitro/In Vivo Correlations; Guidance for Industry; U.S. Department of Health and Human Services, Food and Drug Administration, Center for Drug Evaluation and Research (CDER), U.S. Government Printing Office: Washington D.C. (September 1997)). Hence, four time points were chosen to study the release at 2 hrs, 4 hrs, 6 hrs and 8 hrs.

Figure 2:
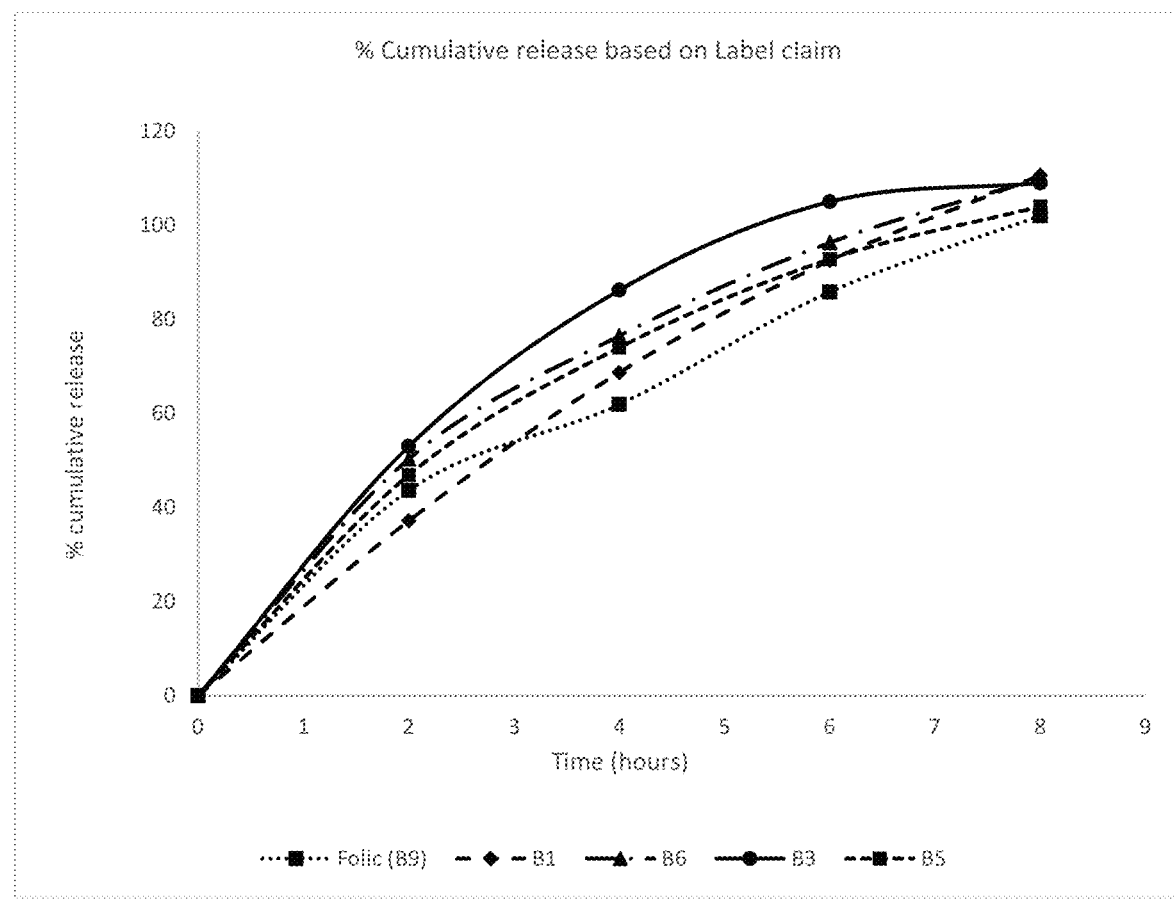
FIG. 2 depicts a graph showing in vitro dissolution percent cumulative release of B vitamins present in the modified release layer of the tablet (percent cumulative release based on label claim).

As seen in FIG. 2, the B vitamins from layer 1 released slowly over 8 hours and the data was found to have less than 10% RSD (biotin was not analyzed). From the immediate release layer, B2 was analyzed and it performed as expected to release around 104% of the label claim. Thus, it was shown that dual-release was achieved from the bi-layer tablet with B2 and B12 released instantly within 1 hour and the remaining 6 B vitamins released slowly over 8 hours. In a future study, the in vivo uptake and bio accessibility will be evaluated in a gastro-intestinal model.

For water-soluble multi-vitamins, USP recommends <2010> testing of one index vitamin and folic acid. This test is required by FDA because of the importance of the relationship between folate deficiency and the risk of neural tube defects. If riboflavin is present, that is selected as the index vitamin because of its limited solubility (Disintegration and Dissolution of Dietary Supplements <2040> in United States Pharmacopoeia and National Formulary (USP 39) Rockville, Md.). Moreover, folic acid is the most sensitive vitamin as it is susceptible to degradation by light and oxygen (Joseph J A Formulation Challenges: Multiple Vitamin and Mineral Dosage Forms. In Augsburger Larry and Hoag Stephen eds. Pharmaceutical Dosage Forms: Tablets, Volume 2 Rational Design and Formulation ($3^{rd}$ ed) New York, N.Y., USA CRC Press (2008); Arcot J: Shrestha A, "Folate: Methods of analysis," *Trends in Food Science and Technology*, (16):253-266 (2005)); therefore, this vitamin was used as a marker vitamin in the formulation.

Basic yeast is natural and can be a source of amino acids and minerals. The basic yeast used as a natural excipient in the formulation contributed to the extended release of the B vitamins from the tablet. Surprisingly, as shown in Table 2, it was observed that the basic yeast in the immediate release layer had an effect on the release of folic acid in the modified release layer. The data demonstrates the effect of basic yeast (present in the immediate release layer) on the release profile of folic acid.

Thus, the data shows that a natural nutritive excipient (in combination with a lower amount of a polymer) can be used in place of other commonly used materials to achieve time release.

The use of basic yeast also helps to keep the polymer levels low and yet obtain the desired time release profile.

After confirming the extended release profile of the five B vitamins from layer 1, further studies were performed only on release of folic acid from the tablet, which can be considered as a representative profile for the extended release profile of the six B vitamins.

Interestingly, it was found that the yeast in the immediate release layer had an effect on the release of folic acid in the time release layer ($1^{st}$ layer). For formulation A1, which did not have any yeast in the $2^{nd}$ layer, the folic acid release was initially much higher. This initial burst release was slowed down as the amount of yeast was increased from 30 to 90 mg in the $2^{nd}$ layer from formulas A2 to A4 (Table 1 and FIG. 3). For all the formulations, the hardness was kept constant.

C. Discussion

Vitamin B complex supplement was formulated to release six B vitamins slowly over eight hours. It was observed that the release profile of each B vitamin depended on its intrinsic solubility. The solubility of an active is a very important factor for the release of active from HPMC extended-release tablet (Nokhodchi A. et al., "The Role of Oral Controlled Release Matrix Tablets in Drug Delivery Systems," *Bioimpacts* 2(4):175-187 (2012)). High-solubility actives can dissolve through the gel matrices, which is considered to be the main pathway for their release. Highly soluble actives also act as pore formers with the formation of micro-cavities and make the gel structure more porous and weaker, increasing in drug or nutrient release. Hence, solubility of the actives can be used to predict the release of actives from controlled release matrix. The solubility of active B vitamins in water is demonstrated in Table 3 (The Merck Index, $13^{th}$ ed Merck and Company, Whitehouse Station, N.J. (2001); Eitenmiller R R, Ye L, Laden W O, "Vitamin Analysis for the health and food sciences," CRC Press: Boca Raton (2008); Ball G F M, "Vitamins in food: analysis, bioavailability and stability," Taylor and Francis: Boca Raton Fla., VOL 156 (2006); Handbook of Vitamins $4^{th}$ ed Zempleni J, Rucker R B, McCormick D B. SJW Eds. CRC Press Boca Raton (2007)).

TABLE 3

Solubility of B vitamins in water

| Actives | Solubility in Water (Per 100 ml water) |
|---|---|
| Niacinamide (B3) | 69.1 g |
| Pyridoxine (B6) | 30.8 g |
| Pantothenic acid (B5) | >10 g |
| Thiamine (B1) mononitrate | 2.7 g |
| Biotin | 0.022 g |
| Folic Acid | 0.016 g |
| Riboflavin (B2) | 0.010 g |

As shown in Table 3, the solubility decreases as Niacinamide (B3)>Pyridoxine (B6)>Pantothenic acid (B5)>Thiamine (B1)>Biotin>Folic acid>Riboflavin. It was observed that the release of actives from the matrix also followed the same order as their intrinsic solubility and was Niacinamide>Pyridoxine>Pantothenic acid>Thiamine>Folic acid. Based on this relation, the release of folic acid and thiamine was used to predict the release of biotin, which was expected to have an intermediate release profile.

This study was first to investigate the effect of basic yeast on the dissolution profile of folic acid from vitamin B dual-release formulations. The commonly used excipients (diluents and fillers) in extended release products are typically non-nutritive manufactured excipients such as microcrystalline cellulose or polyvinylpyrrolidone (PVP). Basic yeast is natural and can be a source of some amino acids and minerals. The basic yeast used as a natural excipient in this product contributed to the extended release of the vitamins from the tablet. Interestingly, it was observed that the yeast in the immediate release layer had an effect on the release of folic acid in the time release layer ($1^{st}$ layer). The data shows that a natural nutritive excipient can be used in place of other commonly used materials to achieve time release. The use of yeast also helps to keep the HPMC levels low and while still obtaining the desired time release profile.

In this system, the instant release layer can act as a surface barrier initially and restrict the surface area available for the release of actives from the time release layer. Due to this control, the burst effect can be reduced and lead to linearization of the drug release profile. Potential mixing of components between the two layers at the interface may also cause localized higher viscosities due to the interaction of the yeast and polymer, further reducing the release rate.

Figure 3:
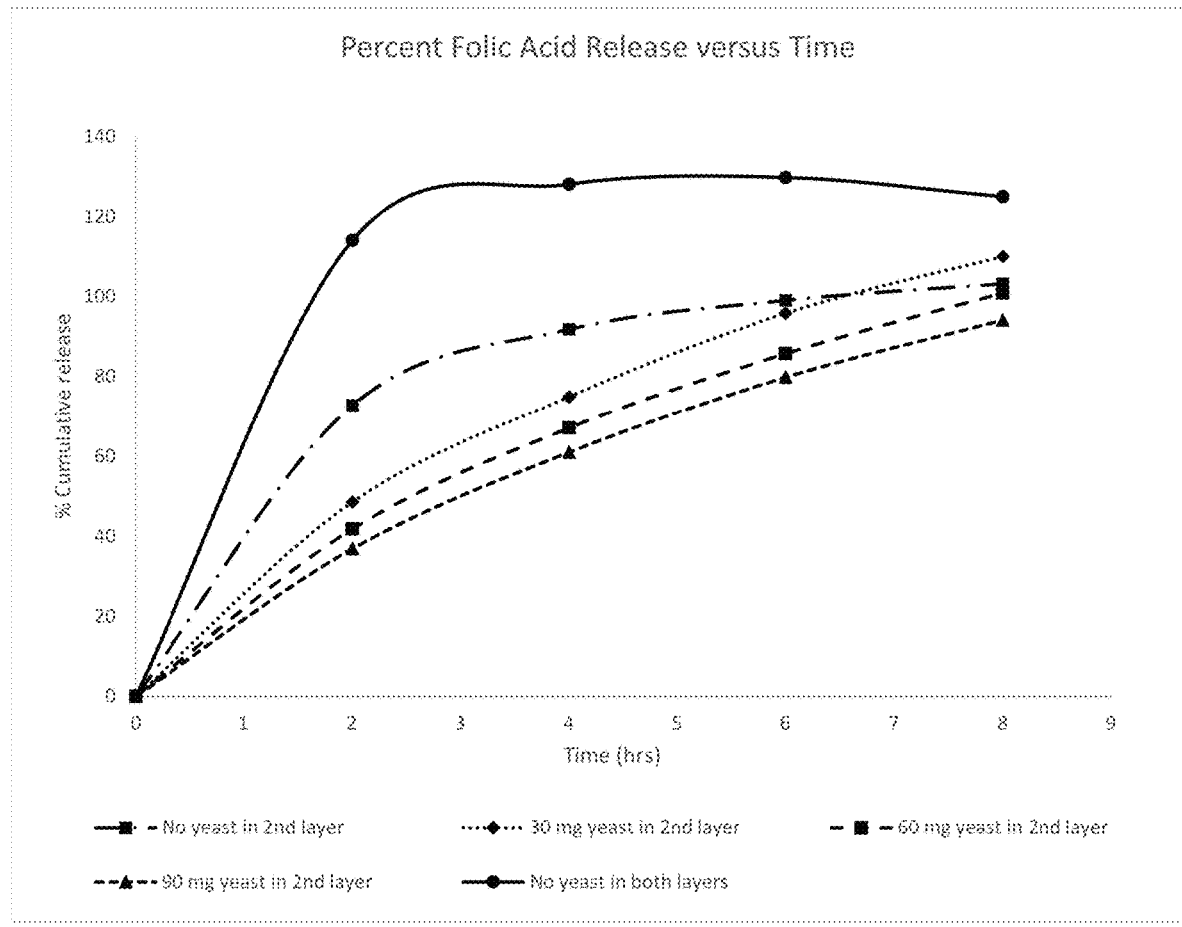
FIG. 3 depicts a graph showing the percent folic release over time.

Yeast consists of many components such as proteins, cell wall glucans, polysaccharides, vitamins, and lipids. Some of the polysaccharides, such as chitin can have gel-like properties. It is believed that when the tablet surface hydrates and the instant release layer undergoes quick erosion, yeast being slightly soluble does not leave the tablet and sticks to the slow releasing layer. The components of yeast contribute to the viscous gel layer forming at the surface. This gel layer formed at the surface due to the presence of yeast in layer 2 helps to reduce the initial burst release as can be seen in FIG. 3. With time, swelling of the polymer causes increase in the diffusional path length of the actives and lowers the release rate. A combination of both these excipients directs the folic acid release in a slow timely manner.

Example 2: Bioaccessibility of Riboflavin from Instant Release vs. Modified Release Formulation The bilayer product of this invention has one layer providing instant release and one layer providing modified (i.e., time) release. The instant release layer can act as a surface barrier and restrict the surface area available for the release of actives from the time release layer. Due to this control, the burst effect can be reduced and lead to linearization of the drug release profile. Potential mixing of components between the two layers at the interface may also cause localized higher viscosities due to the interaction of the yeast and polymer, further reducing the release rate.

Yeast includes many components such as proteins, cell wall glucans, polysaccharides, vitamins, lipids, etc. Some of the polysaccharides such as chitin can have gel-like properties. It is contemplated that when the tablet surface hydrates and the instant release layer undergoes quick erosion, yeast, which is slightly soluble, does not leave the tablet but sticks to the slow releasing layer. The components of yeast contribute to the formation of the viscous gel layer at the surface of the instant release layer. This gel layer helps to reduce the initial burst release as can be seen in FIG. 2. Over time, swelling of the polymer causes an increase in the diffusional path length of the actives and lowers the release rate. A combination of these excipients (basic yeast and polymer) ensures the folic acid release in a slow timely manner.

Bioaccessibility of riboflavin from instant release vs. modified release formulation was investigated.

The immediate and modified release formulations were tested individually to determine the release profile in a dynamic computer-controlled in vitro system simulating the human upper gastrointestinal tract (TIM-1 system).

TABLE 4

Total Bioaccessibility of Riboflavin (B2)

|  | Instant Release (%) | | Modified Release (%) | |
| --- | --- | --- | --- | --- |
|  | High Dose | Low Dose | High Dose | Low Dose |
| Total Bioaccessibility | 88.7 ± 3 | 79.4 ± 0 | 56.3 ± 4.1 | 42.3 ± 6.6 |

TABLE 5

Modified Release % remaining at 5 hours

|  | B1 | B2 | B3 | B5 | B6 | B7 | B9 | B12 |
| --- | --- | --- | --- | --- | --- | --- | --- | --- |
| Low Dose | 25 ± 2.5 | 48.2 ± 8.2 | 12 ± 0.7 | 29.5 ± 5.7 | 36.6 ± 3.4 | 34.9 ± 12.7 | 18.2 ± 7.4 | N/A |
| High Dose | 15 ± 0.7 | 23 ± 2 | 10.9 ± 1.8 | 2.8 ± 0.5 | 7.2 ± 0.5 | 4.1 ± 0.3 | 6.2 ± 0.7 | N/A |

Table 4 shows higher bioaccessibility of B2 from the immediate release tablets (79% for low dose and 89% for high dose) vs. the modified release tablets (42% for low dose and 56% for high dose).

It was also found that B2 had a high percentage of vitamin remaining in the tablet after the course of the 5 hour study, which was especially evident in the low dose formula as 48.2% of the riboflavin was still remaining (Table 5).

From the data, it was concluded that the B2 was best released when incorporated as an instant release nutrient. In support of this design element, peak gut lumen concentrations from instantly released riboflavin remain under measured maximal riboflavin transporter kinetics so efficiency of absorption of this vitamin is maintained by being included in the instant release layer. Maximal vitamin B2 concentration was measured in the TIM-1 system to be approximately 2 micromolar at time 60-120 minutes, which is well below published research demonstrating a maximal permeability concentration for active transport of vitamin B2 at less than 25 micromolar (Zielinska-Dawidziak M, et al., "Transport of high concentration of thiamin, riboflavin and pyridoxine across intestinal epithelial cells caco-2," *J Nutr Sci Vitaminol*, 54:423-429 (2008)).

Example 3: USP Dissolution Study and Toegepast Natuurwetenschappelijk Onderzoek (TNO; as Translated into English, Netherlands Organization for Applied Scientific Research) TIM-1 Study of Nutrilite Global Vitamin B To validate the time release profile and the absorption/bioavailability, a tablet according to the present invention (designated as Nutrilite Global Vitamin B (NF6853) was prepared to have an in vitro release rate that correlated with the TNO TIM-1 study, under simulated human gastrointestinal conditions. In this manner, a Level A in vitro in vivo correlation (IVIVC) was confirmed, and we were able to justify that in vitro dissolution specifications are representative of normal human absorption.

The method developed is described below.

Nutrilite Vitamin B Formula

TABLE 6

Label Claims and Input of B vitamins in Nutrilite Vitamin B Formula

| Active | Label Claim | Units | Overage | Input (mg) |
| --- | --- | --- | --- | --- |
| Thiamine (B1) | 3 | mg | 32.0% | 3.96 |
| Riboflavin (B2) | 3.4 | mg | 35.0% | 4.59 |
| Niacinamide (B3) | 20 | mg | 25.0% | 25 |
| Pantothenic acid (B5) | 20 | mg | 25.0% | 25 |
| Pyridoxine (B6) | 4 | mg | 30.0% | 5.2 |
| Folic acid | 400 | mcg | 40.0% | 560 |
| Biotin | 125 | mcg | 30.0% | 162.5 |
| B12 | 6 | mcg | 35.0% | 8.1 |

Dissolution Release Profile

USP Dissolution Study: To Establish in Vitro Data

Based on USP XXXVI chapter 1088 (which is incorporated herein in its entirety), extended-release tablets are formulated in such a manner as to make the active available over an extended period of time following ingestion.

There is no USP monograph available for multivitamin B extended release tablets. Therefore, it is the responsibility of the formulation scientists to develop an appropriate in vitro dissolution protocol.

TNO Intestinal Model-1 (TIM-1): To Establish in Vivo Data

The best dissolution method for in vivo in vitro correlation is a method that describes what happens in vivo. To determine the in vivo absorption of B vitamins, a TNO study using the TIM-1 apparatus was used as a surrogate to represent the in vivo release of the vitamins from NF6853.

Level A IVIVC of dissolution and TIM-1 data

The Level A IVIVC generally defines a linear relationship between in vitro and in vivo data so the measurement of the in vitro dissolution rate alone is sufficient to determine the pharmacokinetic parameters. For water-soluble multivitamin supplements, USP, Chapter 2040 (recommendations are in Chapter 2040 on disintegration and dissolution in the United States Pharmacopoeia) requires testing of one index vitamin and folic acid.

Results

Dissolution Testing

The dissolution profiles, performed according to USP, Chapter 711, which is incorporated by reference herein in its entirety, representing % label claim and % input for Nutrilite Vitamin B extended-release formulation NF6853 are shown below.

Table 7 shows the percent cumulative release for instant release Riboflavin (B2) based on label claim as well as input from in vitro dissolution testing.

TABLE 7

| Time | % release (LC) | % release (input) |
|---|---|---|
| 1 hour | 104 | 77.12 |

The USP requirement for instant release vitamins is for not less than 75% of label claim to be released within one hour. The dissolution results above show that there is a complete release of riboflavin (B2) within an hour, which meets the USP requirement.

Figure 4:
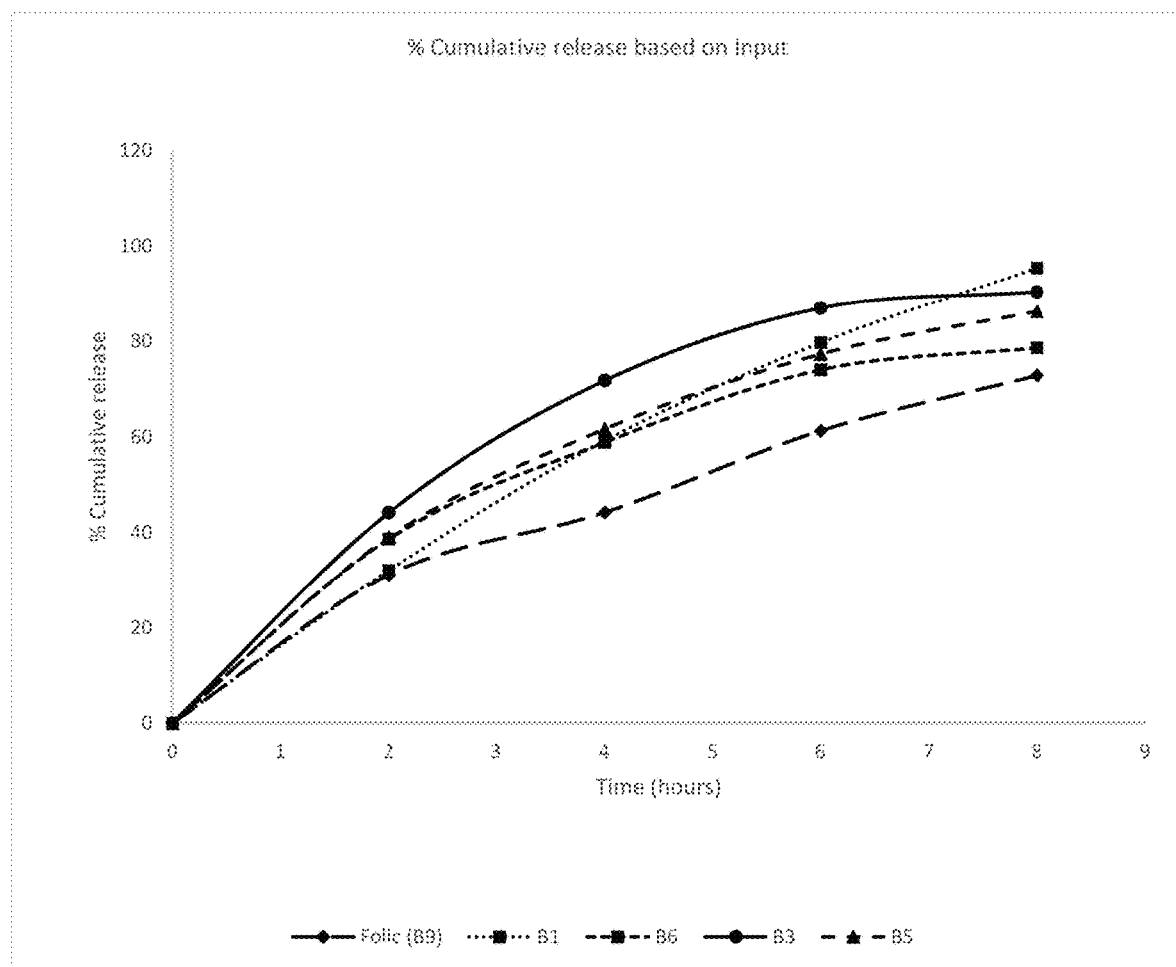
FIG. 4 depicts a graph showing in vitro dissolution percent cumulative release of B vitamins present in the modified release layer of the tablet (percent cumulative release based on input).

FIG. 4 show in vitro dissolution percent cumulative release of B vitamins present in the time release layer of the tablet. (USP <711>) Specifically, FIG. 4 shows cumulative release of B vitamins based on input.

TIM-1 Testing

Figure 5:
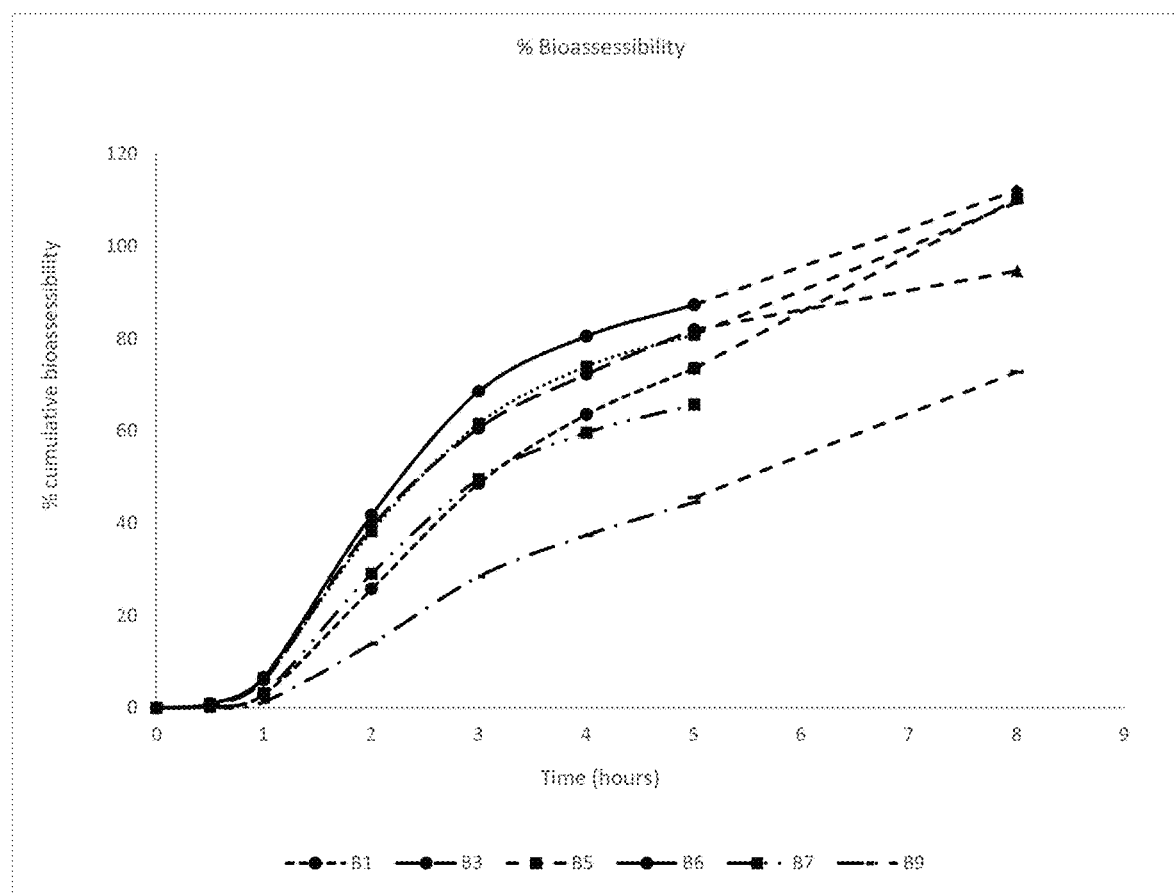
FIG. 5 depicts a graph showing the extended release profile for the B vitamin formula tested in the TNO TIM-1 model.

FIG. 5 shows the extended release profiles for the vitamin B formula tested in the TNO TIM-1 model. Assay data for the release profiles is provided in Table 4 above. Because the TIM-1 system is designed to mimic physiological transit times, the study is performed for 5 hours. The bioaccessibility curves are predicted up to 8 hours using the in vitro dissolution profile (calculated from % input) as shown in FIG. 2. The relationship between TIM-1 data and in vitro dissolution data was found to be linear. The linear equations were used to calculate expected bioaccessibility at 8 hours.

Level A IVIVC

For water-soluble multivitamin supplements, USP recommends (See Chapter 2040 (Table 1) of USP, which is incorporated herein by reference in its entirety) requires testing of one index vitamin and folic acid. If riboflavin is present, then that is selected as the index vitamin. Hence, to determine Level A IVIVC for inventive tablet, folic acid was selected for extended release and riboflavin for instant release correlation.

Figure 6:
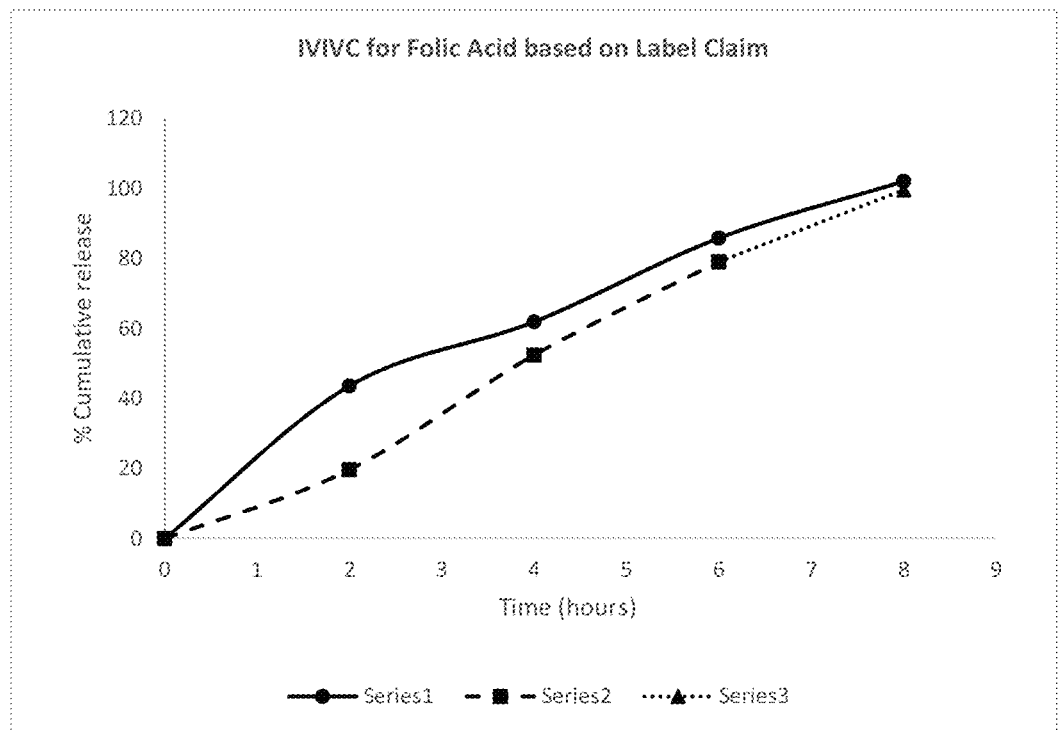
FIG. 6 depicts a graph showing the percent cumulative release, in-vitro in-vivo correlation (IVIVC) for folic acid based on the label claim over time.
Figure 7:
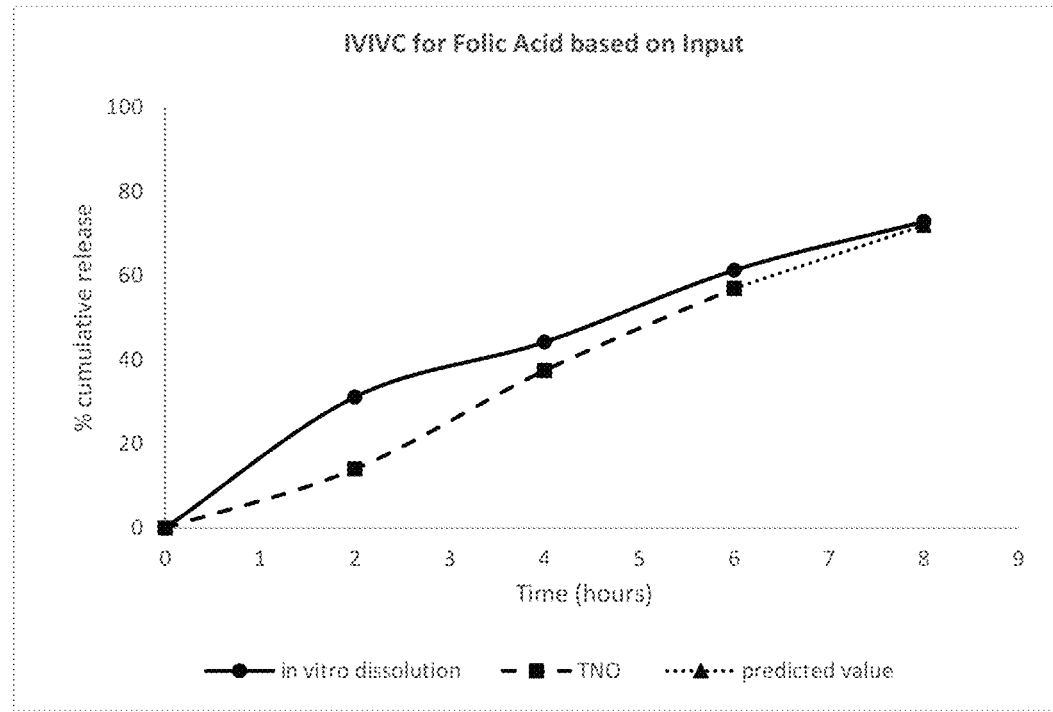
FIG. 7 depicts a graph showing the percent cumulative release, IVIVC for folic acid based on the input over time.

FIG. 6 and FIG. 7 show a point-to-point correlation between the in vitro dissolution data and the TIM-1 data. The lines from each set of data do not completely overlap each other, which is to be expected due to the different testing conditions. The TIM-1 test conditions vary from in vitro dissolution in pH, agitating motion, and total media volume. However, the statistical analysis shows that these data sets are not significantly different (Student T-test, $p=0.76$.)

From this analysis, it was demonstrated that a Level A IVIVC can be established with the in vitro dissolution data and the TIM-1 study. This means that the in vitro dissolution testing procedure is an appropriate method to determine the in vitro performance of the extended-release vitamin B tablet. The extended release layer provides slow release of six B vitamins for about 8 hours.

Example 4: Vitamin B Bilayer Dissolution

Dissolution of folic acid from tablets including basic yeast at 30 mg, 60 mg, and 90 mg in the second or modified release layer was studied over an 8 hour period and compared with the label claim.

Folic Acid dissolution procedure: USP apparatus II used. Media: Phosphate buffer with 1 gram of EDTA to prevent folic acid degradation in media for up to 8 hours (developed by Nutrilite).

Media volume: 500-900 ml
RPM: 50, 75, 100
Temperature: 37° C.

Tablet was placed in a sinker and added to the dissolution vessel. Sample pulled at 2, 4, 6 and 8 hour time points from the vessel.

Figure 8:
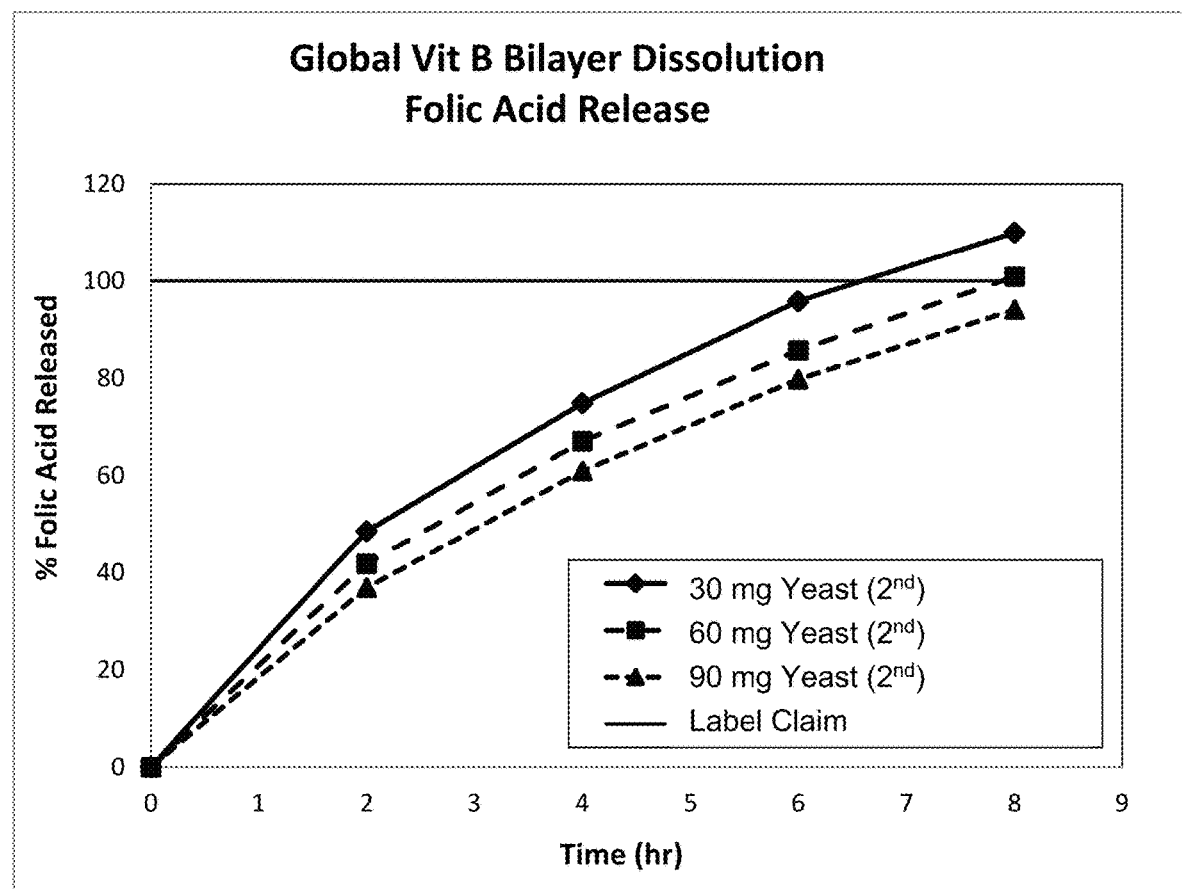
FIG. 8 depicts Vitamin B bilayer dissolution of folic acid release over time.

FIG. 8 shows the results of the study.

Example 5: Home Use Test—Vitamin B Tablet

A study was designed to evaluate digestive comfort for the revised Vitamin B tablet. This study was conducted through a home use test with human subjects for the duration of three days.

A total of 118 individuals were recruited to complete the home use test for Vitamin B. Panelists included 53 males and 65 females with an average age of 44. Panelists were divided into two groups, High Dose Vitamin B and Low Dose Vitamin B. Each group contained 59 panelists.

For description statement questions, respondents rated their agreement/disagreement to the individual product description statement prior to the product evaluation using a 5-point scale: 1=strongly disagree, 2=somewhat disagree, 3=neither agree nor disagree, 4=somewhat agree, and 5=strongly agree.

If the agreement scores (4 and 5 combined) is less than 50%, the percent agreement is calculated as the total percentage of respondents who select 4 or 5 as their response.

If the agreement score (4 and 5 combined) is greater than or equal to 50% without being rounded, then the percentage of respondents that selected 3 as their response (neither agree nor disagree) will be split evenly between the agreement responses (4 and 5) and disagreement responses (1 and 2). If an uneven count of respondents that selected 3 makes it impossible to split evenly, then the extra 1 percentage point will be attributed to the disagreement score during the percent agreement calculation.

A binomial test (sign test) was then performed for the combined agreement group at both the 95% and 90% confidence levels.

Findings from the home use test indicate all claims were substantiated for both Low Dose Vitamin B and High Dose Vitamin B.

Products Tested

TABLE 8

Vitamin B Samples

| Sample Code | Sample Description |
|---|---|
| 312 | Low dose (low potency formula) |
| 683 | High dose (high potency formula) |

The high potency/dose formula included (actives are present in 2-7 of the controlled release layer and 1-2 of the immediate release layer):

The high potency/dose formula included (actives are present in 2-7 of the controlled release layer and 1-2 of the immediate release layer):

| Label Per 1 Tablets | U/M | % EX. | Fnd# | Ingredients |
|---|---|---|---|---|
| Controlled Release Layer: | | | | |
| 45.00 | Mg | 0 | 1 | Benocel K100M (Ashland) |
| 4.00 | Mg | 30 | 2 | Pyridoxine HCl |

The high potency/dose formula included
(actives are present in 2-7 of the controlled release layer and
1-2 of the immediate release layer):

| Label Per 1 Tablets | U/M | % EX. | Fnd# | Ingredients |
|---|---|---|---|---|
| 0.4000 | Mg | 40 | 3 | Folic Acid, USP |
| 3.00 | Mg | 32 | 4 | Thiamine Mononitrate, 97%, Granulation |
| 20.00 | Mg | 25 | 5 | Niacinamide, Granular, USP, DC Powder |
| 20.00 | Mg | 25 | 6 | d-Calcium Pantothenate, USP, |
| 0.125 | Mg | 30 | 7 | Biotin 1% on MCC |
| 30.00 | Mg | 0 | 8 | Direct Compression Yeast (ET Horn) |
| 1.00 | Mg | 0 | 9 | Silicon Dioxide, NF |
| 15.00 | Mg | 0 | 10 | Spirulina |
| 41.350 | Mg | 0 | 11 | Lactose Anhydrous |
| 60.000 | Mg | 0 | 12 | Microcrystalline Cellulose, Silicified |
| 24.80 | Mg | 0 | 13 | MCC, USP |
| 1.50 | Mg | 0 | 14 | Magnesium Stearate, Vegetable |
| Immediate Release Layer: | | | | |
| 0.006 | Mg | 35 | 1 | Vitamin B12 1% on DCP |
| 3.40 | Mg | 35 | 2 | Riboflavin, Fine Powder, USP-FCC |
| 60.00 | Mg | — | 3 | D.C. Yeast (ET Horn) |
| 60.00 | Mg | — | 4 | Spirulina |
| 15.00 | Mg | — | 5 | Microcrystalline Cellulose, Silicified |
| 27.00 | Mg | — | 6 | Lactose Fast Flow |
| 21.60 | Mg | — | 7 | MCC, USP |
| 9.00 | Mg | — | 8 | Croscarmellose Sodium |
| 0.96 | Mg | — | 9 | Silicon Dioxide |
| 1.00 | Mg | — | 10 | Magnesium Stearate, Vegetable |

The low potency formula included (actives are present in 2-7 of the controlled release layer and 1-2 of the immediate release layer):

The low potency formula included
(actives are present in 2-7 of the controlled release layer and
1-2 of the immediate release layer):

| Label Per 1 Tablets | U/M | % EX. | Fnd# | Ingredients |
|---|---|---|---|---|
| Controlled Release Layer: | | | | |
| 64.00 | mg | 0 | 1 | Benecel K100M (HPMC) |
| 1.40 | mg | 25 | 2 | Pyridoxine HCl |
| 0.2000 | mg | 30 | 3 | Folic Acid Trituration 10% |
| 1.10 | mg | 30 | 4 | Thiamine Mononitrate, 97%, Granulation |
| 16.00 | mg | 20 | 5 | Niacinamide, Granular, USP, DC Powder |
| 6.00 | mg | 25 | 6 | d-Calcium Pantothenate, USP, |
| 0.05 | mg | 25 | 7 | Biotin Trituration, 1% |
| 25.00 | mg | 0 | 8 | Direct Compression Yeast (ET Horn) |
| 1.00 | mg | 0 | 9 | Silicon Dioxide, NF |
| 15.00 | mg | 0 | 10 | Spirulina |
| 42.200 | mg | 0 | 11 | Lactose Fast flow |
| 43.000 | mg | 0 | 12 | Microcrystalline Cellulose, Silicified |
| 67.60 | mg | 0 | 13 | Dicalcium Phosphate, unmilled, dihydrate |
| 1.50 | mg | 0 | 14 | Magnesium Stearate, Vegetable |
| Immediate Release Layer: | | | | |
| 0.0025 | mg | 30 | 1 | Vitamin B12 0.1% on DCP |
| 1.40 | mg | 30 | 2 | Riboflavin, Fine Powder, USP-FCC |
| 60.00 | mg | — | 3 | D.C. Yeast |

The low potency formula included
(actives are present in 2-7 of the controlled release layer and
1-2 of the immediate release layer):

| Label Per 1 Tablets | U/M | % EX. | Fnd# | Ingredients |
|---|---|---|---|---|
| 65.00 | mg | — | 4 | Spirulina |
| 16.00 | mg | — | 5 | Microcrystalline Cellulose, Silicified |
| 28.70 | mg | — | 6 | Lactose Fast flow |
| 36.50 | mg | — | 7 | Dicalcium Phosphate, unmilled, dihydrate |
| 11.30 | mg | — | 8 | Croscarmellose sodium |
| 1.20 | mg | — | 9 | Silicon Dioxide |
| 1.20 | mg | — | 10 | Magnesium Stearate, Vegetable |

The High Dose Vitamin B claims had consistently lower top two box score percentages than the Low Dose Vitamin B. These results indicate that for digestive comfort the Low Dose Vitamin B is slightly preferred over the High Dose Vitamin B.

TABLE 9

Claims table for Low and High Dose Vitamin B

| Sample | Question | Top 2 Box w Neutral % | Pass/Fail at 95% Confidence Interval |
|---|---|---|---|
| 312 Low Intensity | This tablet is not gentle on my stomach. | 89.29%** | Pass |
| 312 Low Intensity | This tablet is easy on my stomach. | 91.07% | Pass |
| 312 Low Intensity | This tablet is easy on my digestion. | 92.86% | Pass |
| 312 Low Intensity | This tablet causes no stomach upset. | 91.07% | Pass |
| 312 Low Intensity | This tablet causes digestive upset. | 91.07%** | Pass |
| 312 Low Intensity | This tablet is stomach friendly. | 91.07% | Pass |
| 683 High Intensity | This tablet is not gentle on my stomach. | 84.75%** | Pass |
| 683 High Intensity | This tablet is easy on my stomach. | 86.44% | Pass |
| 683 High Intensity | This tablet is easy on my digestion. | 88.14% | Pass |
| 683 High Intensity | This tablet causes no stomach upset. | 84.75% | Pass |
| 683 High Intensity | This tablet causes digestive upset. | 91.53%** | Pass |
| 683 High Intensity | This tablet is stomach friendly. | 86.44% | Pass |

**These scores were reversed due to the negative nature of the question

Throughout this specification various indications have been given as preferred and alternative embodiments of the invention. However, the foregoing detailed description is to be regarded as illustrative rather than limiting and the invention is not limited to any one of the preferred embodiments. It should be understood that it is the appended claims, including all equivalents that are intended to define the spirit and scope of this invention.

The invention claimed is:

1. A bilayer multi-B vitamin formulation comprising:
   a. a first layer comprising basic yeast at an amount of about 30 mg to about 90 mg, and a set of B vitamins comprising riboflavin (B2) and cyanocobalamin (B12), the first layer providing immediate release of the first set of B vitamins at a first location in the gastrointestinal tract;

b. a second layer comprising basic yeast and a folic acid, the second layer providing a modified release of the folic acid at a second location in the gastrointestinal tract;

wherein the basic yeast from the first layer upon administration to a subject, contributes to the modified release of the folic acid from the second layer;

wherein the first and the second layers of the bilayer multi-B vitamin formulation each comprise abutting substantially planar layers which form the bilayer tablet; and c. optionally, a film coating that covers the first layer and the second layer.

2. The bilayer multi-B vitamin formulation of claim 1, wherein the basic yeast modulates the dissolution profile of the folic acid from the formulation.

3. The bilayer multi-B vitamin formulation of claim 1, wherein the modified release of the folic acid from the second layer is over a period of 8 hours.

4. The bilayer multi-B vitamin formulation of claim 1, wherein the formulation is for oral delivery.

5. The bilayer multi-B vitamin formulation of claim 1, wherein the formulation is in a form of a tablet.

6. The bilayer multi-B vitamin formulation of claim 1, wherein the amount of the basic yeast in the first layer is in the range of about 1-90% relative to the weight of the first layer.

7. The bilayer multi-B vitamin formulation of claim 1, wherein the amount of the basic yeast in the second layer is in the range of about 1-90% relative to the weight of the second layer.

8. The bilayer multi-B vitamin formulation of claim 1, wherein upon hydration of a surface of the formulation a viscous gel layer forms at the surface.

9. The bilayer multi-B vitamin formulation of claim 1, wherein the first location in the gastrointestinal tract is selected from the group consisting of the stomach, and the duodenum.

10. The bilayer multi-B vitamin formulation of claim 1, wherein the second location in the gastrointestinal tract is selected from the group consisting of the duodenum, the small intestine, and the large intestine.

11. The bilayer multi-B vitamin formulation of claim 1, wherein the first layer further comprises a polymer selected from the group consisting of hydroxypropyl methylcellulose (HPMC), polyethylene oxide (PEO), hydroxyethyl cellulose, and polyacrylic acid.

12. The bilayer multi-B vitamin formulation of claim 1, wherein the second layer further comprises a polymer selected from the group consisting of hydroxypropyl methylcellulose (HPMC), polyethylene oxide (PEO), hydroxyethyl cellulose, and polyacrylic acid.

13. The bilayer multi-B vitamin formulation of claim 12, wherein the second layer comprises about 12-15% hydroxypropyl methylcellulose.

14. A modified release tablet comprising:
a. a first layer comprising basic yeast at an amount of about 30 mg to about 90 mg, and a first set of B vitamins comprising riboflavin (B2) and cyanocobalamin (B12), the first layer providing immediate release of the first set of B vitamins at a first location in the gastrointestinal tract;

b. a second layer comprising basic yeast and folic acid, the second layer providing a modified release of the folic acid at a second location in the gastrointestinal tract;

wherein the basic yeast from the first layer upon administration to a subject, contributes to the modified release of the folic acid from the second layer;

wherein the first and the second layers of the modified release tablet each comprise abutting substantially planar layers which form the modified release tablet; and c. optionally, a film coating that covers the first layer and the second layer.

15. A dietary supplement comprising a bilayer multi-active formulation comprising:
a. a first layer comprising a basic yeast at an amount of about 30 mg to about 90 mg, and a set of active components, the first layer providing immediate release of the set of active components at a first location in the gastrointestinal tract;

b. a second layer comprising a basic yeast and folic acid, the second layer providing a modified release of the folic acid;

wherein the basic yeast from the first layer upon administration to a subject, contributes to the modified release of the folic acid from the second layer at a second location in the gastrointestinal tract;

wherein the first and the second layers of the dietary supplement each comprise abutting substantially planar layers which form the bilayer multi-active formulation; and c. optionally, a film coating that covers the first layer and the second layer.

16. The bilayer multi-B vitamin formulation of claim 1, wherein the second layer further comprises at least one other B vitamin selected from the group consisting of biotin, niacinamide (B3), pyridoxine (B6), pantothenic acid (B5), thiamine (B1), or a combination thereof, the second layer providing a modified release of the at least one other B vitamin at the second location in the gastrointestinal tract.

17. The bilayer multi-B vitamin formulation of claim 16, wherein the B vitamins are present in amounts within the range from about 0.01 mg to 1000 mg in single or divided doses.

18. The bilayer multi-B vitamin formulation of claim 16, wherein the formulation comprises 1-5 mg of B1, 1-10 mg of B2, 15-30 mg of B3, 5-30 mg of B5, 1-5 mg of B6, 200-500 µg of folic acid, 20-200 µg of biotin, and 1-10 µg of B12.

19. The modified release tablet of claim 14, wherein the second layer further comprises at least one other B vitamin selected from the group consisting of biotin, niacinamide (B3), pyridoxine (B6), pantothenic acid (B5), thiamine (B1), or a combination thereof, the second layer providing a modified release of the at least one other B vitamin at the second location in the gastrointestinal tract.

20. The dietary supplement of claim 15, wherein the second layer of the bilayer multi-active formulation further comprises at least one other B vitamin selected from the group consisting of biotin, niacinamide (B3), pyridoxine (B6), pantothenic acid (B5), thiamine (B1), or a combination thereof, the second layer providing a modified release of the at least one other B vitamin at the second location in the gastrointestinal tract.

\* \* \* \* \*

UNITED STATES PATENT AND TRADEMARK OFFICE
CERTIFICATE OF CORRECTION

PATENT NO. : 11,291,683 B2
APPLICATION NO. : 15/471619
DATED : April 5, 2022
INVENTOR(S) : Chang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 410 days.

Signed and Sealed this
Twenty-ninth Day of November, 2022

Katherine Kelly Vidal
*Director of the United States Patent and Trademark Office*